(12) United States Patent
Carlsson et al.

(10) Patent No.: US 6,902,889 B1
(45) Date of Patent: Jun. 7, 2005

(54) ANALYTICAL METHOD AND ADVICE

(75) Inventors: Jan Carlsson, Uppsala (SE); Maria Lönnberg, Knivsta (SE)

(73) Assignee: Pharmacia Diagnostics AB, Uppsala (SE)

( * ) Notice: Subject to any disclaimer, the term of this patent is extended or adjusted under 35 U.S.C. 154(b) by 0 days.

(21) Appl. No.: 09/633,111

(22) Filed: Aug. 4, 2000

Related U.S. Application Data

(60) Provisional application No. 60/148,566, filed on Aug. 13, 1999, and provisional application No. 60/164,147, filed on Nov. 8, 1999.

(30) Foreign Application Priority Data

Aug. 6, 1999 (SE) .............................................. 9902855
Nov. 1, 1999 (SE) .............................................. 9903970

(51) Int. Cl.[7] .............................................. G01N 33/53
(52) U.S. Cl. .................. 435/6; 435/7.1; 435/287.9; 435/288.3; 436/518; 436/528; 436/530; 436/161; 436/162
(58) Field of Search .............................. 435/7.1, 287.9, 435/288.3; 436/518, 528, 530, 161, 162

(56) References Cited

U.S. PATENT DOCUMENTS

| 4,313,906 A | 2/1982 | Filipi et al. |
| 4,469,601 A | 9/1984 | Beaver et al. |

FOREIGN PATENT DOCUMENTS

| JP | 3154641 | 7/1991 |
| WO | WO9316382 | 8/1993 |
| WO | WO9504280 | 2/1995 |
| WO | WO9530903 | 11/1995 |
| WO | WO9904267 | 1/1999 |
| WO | WO9930145 | 6/1999 |

OTHER PUBLICATIONS

Stedman's Medical Dictionary. 26th Edition.Williams & Wilkins. 1995. p. 336.*

* cited by examiner

Primary Examiner—Bao-Thuy L. Nguyen
(74) Attorney, Agent, or Firm—Dinsmore & Shohl LLP

(57) ABSTRACT

The invention relates to an analytical chromatographic method which comprises the steps of:
  a) providing a membrane type flow matrix attached to a liquid-impervious backing, which flow matrix permits a capillary force assisted lateral fluid flow therethrough, and at least a part of which flow matrix contains ion-exchange functions;
  b) treating the flow matrix to reduce or eliminate unspecific adsorption properties of the flow matrix;
  c) applying to the flow matrix a sample containing at least two components;
  d) initiating a first lateral flow of aqueous fluid to transport the sample through the flow matrix and separate said components therein;
  e) interrupting the lateral flow; and either
  f1) detecting at least one of the separated components on the flow matrix in the position reached by the respective component when the flow was interrupted; or
  f2a) initiating a second flow of aqueous fluid to transport the components in a direction substantially transverse to the direction of the first lateral flow;
  f2b) interrupting the second lateral flow; and
  f2c) detecting at least one of the separated components on the flow matrix in the position reached by respective component when the flow was stopped.

Figure 1:
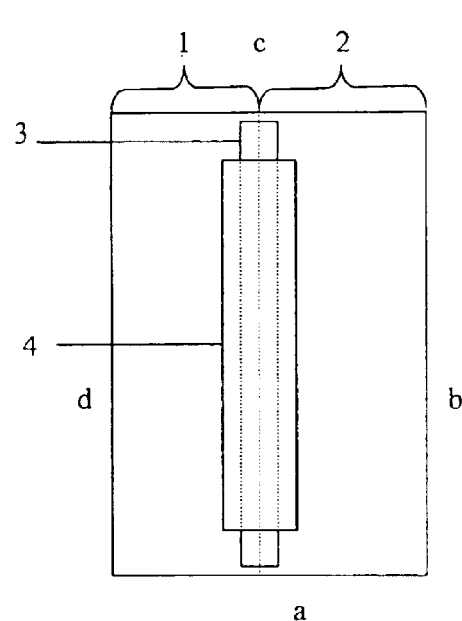

The invention also relates to a chromatographic device comprising a membrane type flow matrix attached to a liquid-impervious backing, which membrane permits a capillary force assisted lateral fluid flow therethrough and at least a part of which is modified to support ion-exchange functions.

23 Claims, 4 Drawing Sheets

ANALYTICAL METHOD AND ADVICE

This application claims priority on provisional Application No. 60/148,566 filed on Aug. 13, 1999, and provisional Application No. 60/164,147 filed on Nov. 8, 1999, the entire contents of which are hereby incorporated by reference.

TECHNICAL FIELD OF THE INVENTION

The present invention relates to a method of determining one or more components in a sample, wherein the sample components are separated by chromatography prior to the determination. The invention also relates to a device therefor.

BACKGROUND OF THE INVENTION

The analysis of complex mixtures of biomolecules usually involves chromatographic or electrophoretic steps and are generally tedious, time-consuming and costly. Often, the analysis of complex mixtures has required combinations of selective extractions and chromatographic separations.

A widely used commercial analytical system for analysing complex mixtures of biomolecules is the PhastSystem™ (Amersham Pharmacia Biotech AB, Sweden) which is an analytical system based on electrophoresis on pre-prepared gels. While this system heavily facilitates the labour and time for the analytical operator, the system is still rather laborious and expensive.

U.S. Pat. No. 4,469,601 discloses a method and system for multi-dimensional chromatography in a thin-layer chromatographic plate wherein a sample is separated into an array of constituents. These constituents are then separated into a second array of sub-constituents by pumping a fluid through the plate in a direction crossing the array, and the sub-constituents are detected as they flow past fixed positions in this second direction. Thin layer chromatography is, however, restricted to the separation of small (i.e. low molecular weight) molecules, and does not permit the separation of biomolecules, such as proteins, for example.

Pristoupil, T. I., Chromatog. Rev., 12 (1970) 109–125 describes the use of nitrocellulose filters in chromatography and electrophoresis. Chromatography in aqueous solution was performed with a nitrocellulose membrane in a horizontal position in a plexiglass chamber. Proteins were detected by immersing the membrane in a staining solution, and other substances were detected by usual spray or sandwich techniques. On the intact membrane, proteins having a molecular weight of the order of $10^5$ and higher were firmly adsorbed on the membrane while peptides, amino acids and other low-molecular substances of hydrophilic character migrated with the front of the developing solution. For electrophoresis, it was necessary to impregnate the membrane with neutral detergents to prevent the high adsorption of proteins. Also immunochromatography of rabbit anti-bovine serum and immunochemically inactive normal rabbit serum on a membrane with bovine serum adsorbed thereto is described. The antigen-antibody complex gave a distinct spot at the start, while the immunochemically inactive proteins migrated without any marked adsorption. Thus, no "true" chromatography of components seems to have been obtained neither in the intact (or plain) membrane nor in the antibody-coated membrane but rather either firm binding or no binding at all.

SUMMARY OF THE INVENTION

It is an object of the present invention to provide an analytical method for the determination of components, especially for determining one or more biomolecules in complex mixtures thereof, which is simpler, faster and cheaper to perform than the prior art methods.

According to the present invention, it has now surprisingly been found that this and other objects and advantages may be obtained by chromatography in thin membranes, e.g. of nitrocellulose, if the membranes have been modified to support ion-exchange functions. It could not be expected from the results presented by Pristoupil, T. I. above (strong non-specific adsorption of proteins or elimination of protein adsorption by detergents) that it would be possible to obtain a pure ion-exchange chromatographic on thin membranes. The separated components may be detected directly on the membrane or after transfer by a cross-flow of liquid to a parallel section of the membrane without ion-exchange functions or to another membrane joined thereto.

Therefore, in one aspect, the present invention provides a chromatographic assay method for qualitative, semi-quantitative or quantitative analysis, which method comprises the steps of:

a) providing a membrane type flow matrix attached to a liquid-impervious backing, which flow matrix permits a capillary force assisted lateral fluid flow therethrough, and at least a part of which flow matrix contains ion-exchange functions;

b) treating the flow matrix to reduce or eliminate unspecific adsorption properties of the flow matrix;

c) applying to the flow matrix a sample containing at least two components;

d) initiating a first lateral flow of aqueous fluid to transport the sample through the flow matrix and separate said components therein;

e) interrupting said lateral flow; and either f1) detecting at least one of said separated components on the flow matrix in the position reached by the respective component when the flow was interrupted; or f2a) initiating a second flow of aqueous fluid to transport the components in a direction substantially transverse to the direction of the first lateral flow;

f2b) interrupting said second lateral flow; and f2c) detecting at least one of said separated components on the flow matrix in the position reached by the respective component when the flow was interrupted.

In another aspect, the present invention therefore provides a chromatographic device comprising a membrane type matrix attached to a liquid-impervious backing, which membrane permits a capillary force assisted lateral fluid flow therethrough and at least a part of which is modified to support ion-exchange functions.

In still another aspect, the present invention provides an apparatus for determining components in a sample, which apparatus comprises a chromatographic device as above, and means for initiating and maintaining a liquid flow through the membrane.

DETAILED DESCRIPTION OF THE INVENTION

As described above, the present invention is based on ion-exchange chromatography of a sample on thin membranes with a liquid tight backing and detection of one or more of the separated components of the sample directly on the membrane, or optionally after transverse liquid transport of the components to another part of the membrane or to another membrane joined thereto without ion-exchange functions. While the sample may contain several (two or more) components, it may sometimes be of interest only to detect and determine one or a few of the separated components.

Membrane

The membrane should have a fine foam-like structure and a standardized narrow distribution of pore sizes, typically in the range of 0.01 to 100 $\mu$m, preferably 0.01 to 20 $\mu$m. The inner surface of the flow channels or pores in the membrane should, of course, be sufficiently hydrophilic to permit aqueous media, such as buffer, serum, plasma, blood, saliva, etc to be transported through the matrix. This transport may be achieved by capillary forces in the matrix itself, but is usually achieved by auxiliary means, such as an absorbent pad of cellulose or the like. The membrane material is usually polymeric, and exemplary polymers are nitrocellulose, polyester, polyethersulphone, nylon, cellulose nitrate, and regenerated cellulose. The membrane thickness is usually less than about 500 $\mu$m, e.g. in the range of from about 25 to about 500 $\mu$m, and preferably less than about 150 $\mu$m, e.g. in the range of from about 75 to about 150 $\mu$m.

The homogeneity of a chromatographic material affects its chromatographic quality and may therefore be reflected in terms of theoretical plate height. The lower height of the theoretical plate, the better the material. The membrane for use in the present invention should thus have a height of theoretical plate (HETP) of less than about 500 $\mu$m, preferably less than about 100 $\mu$m.

The ion-exchange ligands that make the chromatograhic separation in the membrane possible may be anionic, cationic or amphoteric, and may be physically introduced into the matrix in the manufacturing process, or may be anchored to the membrane, either by covalent binding to the membrane, or via physical adsorption. The anchorage of the ion-exchange ligands to the membrane may take place via a polymer or other substituent which in turn carries covalently, physically adsorptively, or biospecifically bound ligands. Another possibility is deposition of polymer particles which exhibit a desired type of ion-exchange ligand. The particles may be of hydrophilic or hydrophobic character, and the ligand structure may be exhibited by a compound adsorbed or covalently bound to the particles. Regarding the technique for binding an ion-exchange ligand to the matrix, it may, for example, be referred to our previously filed International (PCT) applications WO 99/36780, WO 99/36776 and WO 99/36777 (the disclosures of which are hereby incorporated by reference herein).

The ligand density (substitution degree) is selected to obtain the desired isocratic separation. Optionally, the membrane may have different ligand densities or a gradient of ligand densities along the separation direction. The use of a polybuffer with the ion-exchange membrane permits separation by chromatofocusing, in which a pH gradient is formed in the membrane.

Examples of ion-exchange functional groups include anion exchangers, such as diethyl aminoethyl (DEAE), trimethyl hydroxypropyl (QA), quaternary aminoethyl (QAE), quaternary aminomethyl (Q), diethyl-(2-hydroxypropyl)-aminoethyl, triethyl aminomethyl (TEAE), triethylaminopropyl (TEAP), polyethyleneimine (PEI), and cation-exchangers, such as methacrylate, carboxymethyl (CM), orthophosphate (P), sulfonate (S), sulfoethyl (SE), sulfopropyl (SP).

After the ligand coating, the membrane is treated with a detergent or other suitable agent to substantially reduce or eliminate undesired background or unspecific adsorption effects of the membrane matrix as is per se known in the art.

The sample containing the analyte or analytes to be determined may be added directly on the membrane surface, but usually it is added to a separate sample application membrane or pad in liquid contact with the membrane, either in edge to edge contact therewith or, preferably, mounted on top of the membrane.

The conditions for the separation of the components in the membrane are generally isocratic or with stepwise or continuously changed ion-strength.

Detection

Detection and quantification of separated components in the detection zone may take place in various ways. If the separated component or components to be determined are enzymatically active, they may be detected directly by their action on a suitable substrate, e.g. a colour change. Usually, however, detection is performed by protein staining, lipid staining, carbohydrate staining or DNA-staining, or by a biospecific detectable reagent. Such a substrate or reagent may be added via a fluid flow in the matrix, either (i) from one of the membrane sides transverse to the separation direction of the membrane, or (ii) from one of the sides extending in the separation direction of the membrane, or (iii) on top of the membrane. Excess of substrate or reagents will be removed by a buffer flow. Alternatively, the substrate or reagent may be added by incubating the membrane in a solution or suspension thereof wherupon the excess is washed away. Another alternative is spraying the substrate or reagent onto the membrane.

Usually, the separated components are immobilized in the membrane prior to detection as is per se well known in the art, e.g. chemically by a cross-linking agent, such as glutaraldehyde. Other means of immobilization are e.g. denaturation by heating or exposure to an organic solvent.

Enzymatic detection may be performed by conventional methods, for example, as described in "Detection of Enzymes on Electrophoresis Gels: A Handbook", CRC Press Inc., 1994; Electrophoresis of Enzymes: Laboratory methods, G. M. Rothe, ed., Springer Verlag, New York, 1994; and Practical Protein Elctrophoresis for Genetic Research, Timber Press Inc. 1992.

Staining for proteins may be performed by conventional methods, for example with AuroDye or India Ink as described in K. W. Li et al., Anal. Biochem. 182, 44–47 (1989).

Staining for lipids may be performed by conventional methods, for example with Oil Red O, Sudan Black B or Fat Red 7b as described in G. Bittolo-Bon and G. Cazzalato, J. Lipid Res. 40, 170–176 (1999); and in Ö. Gaal et al., Electrophoresis in the Separation of Biological Macromolecules, John Wiley & Sons, 1980, pp. 327–335.

Staining for carbohydrates may be performed by conventional methods, for example as described in A. H. Wardi and G. A. Michos, Anal. Biochem. 49, 607–609 (1972); and G. Dubray and G. Bezard, Anal. Biochem. 119, 325–329 (1982).

The biospecific detectable reagent may be a biospecific affinity reactant which is labelled with an analytically detectable group, such as an enzymatically active group (e.g. colour formation upon action on substrate), fluorescent group, chromogenic group, hapten, biotin, radiolabel (autoradiography), particles, etc. A usual form of analytically labelled reactants is labelled antibody.

A particularly useful labelling group is particles, for example black-coloured carbon particles which may be measured directly, e.g. with a conventional type scanner. Optionally, the particles contain one of the above mentioned detectable groups, such as fluorophoric group or chromogenic group (fluorescent and coloured particles, respectively). Useful particles often have a size in the range 0.001 to 5 μm, with preference for the range 0.05 to 5 μm. The particles may be of colloidal dimensions, so-called sol (i.e. usually spherical and monodisperse having a size in the range 0.001 to 1 μm). Especially may be mentioned metal particles (for example, gold sol), non-metal particles (for example $SiO_2$, carbon, latex and killed erythrocytes and bacteria). Also particles of non-colloidal dimensions have been used. These have been more or less irregular and more or less polydisperse (for example, carbon particles <1 μm; see e.g. our WO 96/22532).

When particles are the label group, the complexes formed in the detection zone may often be detected visually or by optical measuring equipment (e.g. a CCD camera coupled to a computer with special software for image analysis or laser scanner).

For particles as label group, it may further be referred to e.g. WO 88/08534 (Unilever); U.S. Pat. No. 5,120,643 (Abbott Labs.); EP-A-284,232 (Becton Dickinson).

Sometimes, the ion-exchange membrane may not permit detection directly thereon (e.g. due to a particular ion-exchange group). In such a case, it may be necessary to provide a parallel differently or unmodified membrane section, or another membrane joined thereto, to which the separated components may be forced to migrate by a transverse liquid flow initiated after completed separation in the ion-exchange membrane. Such a detection procedure is described in the illustrative embodiment and the specific Example below.

Sample

The analytical method of invention is well suited for the analysis of biological samples, for example, blood (serum, plasma, whole blood), saliva, tear fluid, urine, cerebrospinal fluid, sweat, etc. The invention is also applicable to other types of samples, such as fermentation solutions, reaction mixtures, etc. Sample components that it may be desired to determine are usually high-molecular components, e.g. proteins, peptides, nucleic acids, or polynucleotides.

In addition to treating the membrane to reduce or eliminate non-specific interactions with the membrane, as mentioned above, it may be beneficial, and sometimes even necessary, to add one or more agents to the sample to further reduce such interactions. The amounts of such agent or agents must, however, not be so high that the agent interferes with the ion-exchanging properties of the membrane.

Illustrative Embodiment

In order to facilitate the understanding of the present invention, an embodiment thereof will now be described in more detail, by way of example only, with reference to FIGS. 1 and 2A to 2C of the drawings.

FIG. 1 illustrates schematically a membrane that may be used for the analysis of e.g. proteins in accordance with the method of the invention. The membrane consists in the illustrated case of two combined parts of different materials, a separation part 1 and a detection part 2, joined by a piece of adhesive tape (not shown) on the backside of the combined membrane and in liquid receiving contact with each other by a thin membrane band 3 as an overlap. This membrane band 3 is secured to the separation/detection membrane by a piece of adhesive tape 4. The separation part defines a separation zone on the combined membrane. Likewise, the detection part defines a detection zone on the combined membrane. The short-sides of the membrane are indicated in FIG. 1 by a and c and the long-sides by b and d, respectively.

Figure 2A:
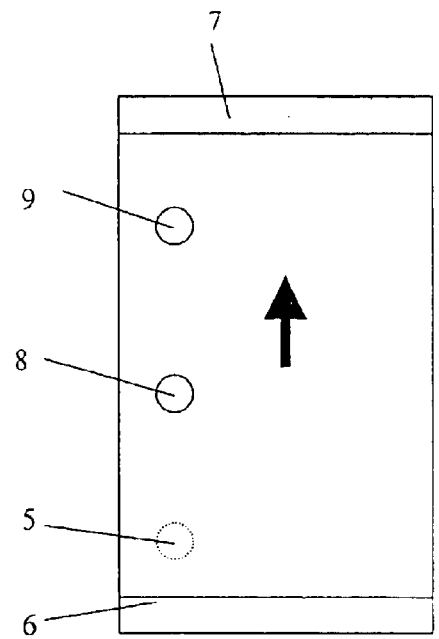

The membrane may be used as follows with reference to FIGS. 2A to 2C. After wetting the membrane, a sample containing two components to be analysed (referred to as analytes 1 and 2 below) is applied at 5 on the separation zone 1 (FIG. 2A). A pad 6 containing separation buffer is applied at short-side a of the membrane and a sucking pad 7 at the opposite short-side c. This will cause a buffer flow of in the direction of the arrow in FIG. 2A, separating the two analytes as indicted by the dots at 8 (analyte 1) and 9 (analyte 2) in FIG. 2A.

Figure 2B:
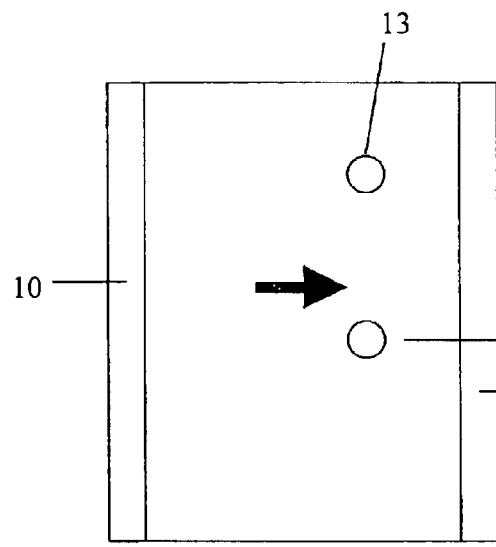

With reference now to FIG. 2B, pads 6 and 7 in FIG. 2A are then removed and an eluent-containing pad 10 is mounted to the long-side d, and a sucking pad 11 is mounted to long-side b. This causes a flow of eluent in the direction of the arrow in FIG. 2B, transporting the separated analytes to positions 12 and 13 in the detection zone where the analytes optionally are immobilized by chemical crosslinking, for example.

Figure 2C:
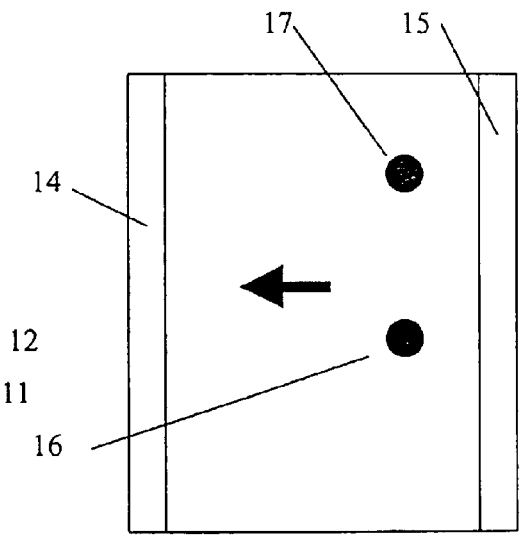

Then, with reference to FIG. 2C, the pads 10 and 11 (in FIG. 2B) are removed and replaced by a sucking pad 14 at the long-side d, and a container 15 with a solution or suspension of labelled reactant at the long-side b. Thereby, labelled reactant will migrate in the direction of the arrow and bind to the immobilized analytes at 16 and 17 in FIG. 2C. The labelled complexes, and thereby the corresponding analytes, may then be detected and quantified by reading the intensity of the signals from the label in the detection area and calculating the respective amounts. In case the label is carbon particles, the measurements may advantageously be performed with a scanner.

The above described manual initiation and stopping of the flows are, of course, only given for purpose of illustration, and more sophisticated means therefor are readily apparent to a person skilled in the art, such as so-called imprinted liquid circuits (see e.g. WO 93/10457) etc.

A specific example where the method of the present invention is used for the analysis of asialo-transferrin and bovine albumin is described below.

EXAMPLE

Preparation of Separation Membrane with Anion-Exchange Properties

A sheet of nitrocellulose membrane (3 μm, nitrocellulose on polyester backing, Whatman international Ltd, England) was placed in a solution of 0.1% polyethyleneimine (PEI, Sigma, St Louise, Mo., USA). The mixture was shaken for three hours and the membrane was then placed in 0.1% Tween 20 for 30 minutes, dried in air and then stored in a plastic bag at +4° C.

Preparation of Combination Membrane

The separation membrane was cut to 1.5×5 cm and a plain nitrocellulose membrane was cut to 3.5×5 cm. The two membranes were put tightly together along the long sides and joined by means of adhesive tape on the underside. A piece of nitrocellulose membrane (0.3 cm×5 cm, AE99, Schleicher and Schuell, Dassel, Germany) was placed on the top side of the two membranes as an overlap. This membrane was anchored by means of a 1×4 cm self-adhesive polyester film (Gelman adhesive polyesterfilm, 3 mil) placed such that 0.5 cm at the short side on the formed combined separation/plain nitrocellulose membrane remained uncovered. Below, the short sides of the combination membrane are referred to as a and c, respectively, and the two long sides as b and d respectively (see FIG. 1).

Preparation of Carbon Black

Carbon black stock solution: 1.5 g of carbon black particles (sp 5, Degussa, Germany) were suspended in 150 ml 5 mM borate buffer, pH 8.4 and sonicated (VibraCell 600 W, 1.5 cm probe) in a plastic beaker for 5 minutes at 100% amplitude and 5+5 seconds pulse. 1.5 ml Tween 20 (Sigma, St Louise, Mo., USA) were added and the solution was sonicated for 5 minutes at 100% amplitude and 5+5 seconds pulse.

Carbon black work solution: 4 ml of 10 mg/ml of carbon black stock solution were diluted in 35 ml 5 mM borate buffer, pH 8.4 and 1.2 ml Tween 20 were added. The solution was sonicated (VibraCell 600 W, micro probe) for 5 minutes at 30% amplitude and 5+5 seconds pulse.

Sample Materials

Asialo transferrin: An iron-saturated prepartion of transferrin (Sigma, St Louise, Mo., USA) was treated with neuraminidase (Behring ORKD, Germany), and asialo transferrin was then isolated by ion-exchange chromatography on Mono Q (Amersham Pharmacia Biotech AB, Sweden).

Bovine albumin: Bovine albumin (Intergen company, Purchase, N.Y., USA) was purified by ion-exchange chromatography on Mono Q (Amersham Pharmacia Biotech AB, Sweden). The most negatively charged part of the material was isolated.

Standard Protocol for Combined Separation and Protein Determination

Step 1. Wetting of Membrane from Short Side a to Short Side c

The combination membrane is wetted by adding elution buffer to 1×5×0.5 cm PVA sponge (PVA D, 60 $\mu$m, Kanebo Ltd, Japan) and then placing the sponge along short side a of the membrane. To the opposed short side c of the membrane is mounted a 2×5 cm sucking cellulose membrane (GB 004, Schlecher and Schuell). When the elution buffer front has reached the cellulose membrane, the PVA sponge is removed. The elution buffer is 20 mM bis-Tris, 0.1% Tween 20, 10 mM NaCl, pH 6.31.

Step 2. Sample Application and Elution from Short Side a to Short Side c 0.5 $\mu$l of sample (0.3–0.7 mg/ml) is placed on the middle of the separation membrane, 1 cm from the short side a. The PVA sponge with elution buffer is added and the elution is continued for 4 minutes. Then the PVA sponge and the sucking membrane are removed. See FIG. 2A.

Step 3. Elution from Long Side d (Separation Membrane) to Long Side b (Detection Membrane)

Along long side b (plain nitrocellulose membrane) is mounted a 2×5 cm cellulose membrane (GB 004, Schlecher and Schuell), and along long side d is placed a 1×5×0.5 cm PVA sponge (PVA D, 60 $\mu$m, Kanebo Ltd, Japan) wetted by elution buffer (20 mM bis-Tris, 1000 mM NaCl, 0.1% Tween 20, pH 6.30). The elution is continued for 5 minutes and the flow is stopped by removing the PVA sponge and the sucking membrane. See FIG. 2B.

Step 4. Immobilising of Proteins

The combination membrane is dried by a hairdryer for about 1–2 minutes. Then the membrane is sprayed with 12.5% glutaraldehyde (Merck), the excess is wiped off and the reaction is continued for 4 minutes.

Step 5. Reaction with Carbon-Black

A 2×5 cm sucking cellulose membrane (GB 004, Schlecher and Schuell) is mounted along long side d (separation membrane part), and along long side b is placed a 1×5×0.5 cm PVA sponge (PVA D, 60 $\mu$m, Kanebo Ltd, Japan) wetted by 1 mg/ml of carbon black in 3% Tween 20. The carbon black particles are allowed to pass the immobilised proteins for 7 minutes and then the PVA sponge is replaced with an identical PVA sponge filled with elution buffer (see step 1). This washing is continued for 10 minutes and then the PVA sponge and the sucking membrane are removed and the combination membrane is dried.

Step 6. Detection of Blackening

The membrane is placed in a scanner (Agfa Acus II Scanner) for mesurement of the grey scale in a 1 cm broad line along the plain nitrocellulose membrane where the proteins are immobilised and coloured with carbon black. The grey scale is read with a 12 bits grey scale resolution (4096 levels) and 600 points per inch (ppi) optical resolution. The image obtained is digitalised and the intensity values are processed by means of Microsoft Excel. The sum of the pixels intensity in 1 cm of the plain nitrocellulose membrane along the short side of the detection line (10 mm=230 grey scale values) is calculated and the chromatogram for 4 cm along the detection line may be illustrated graphically.

Analyses

Figure 3:
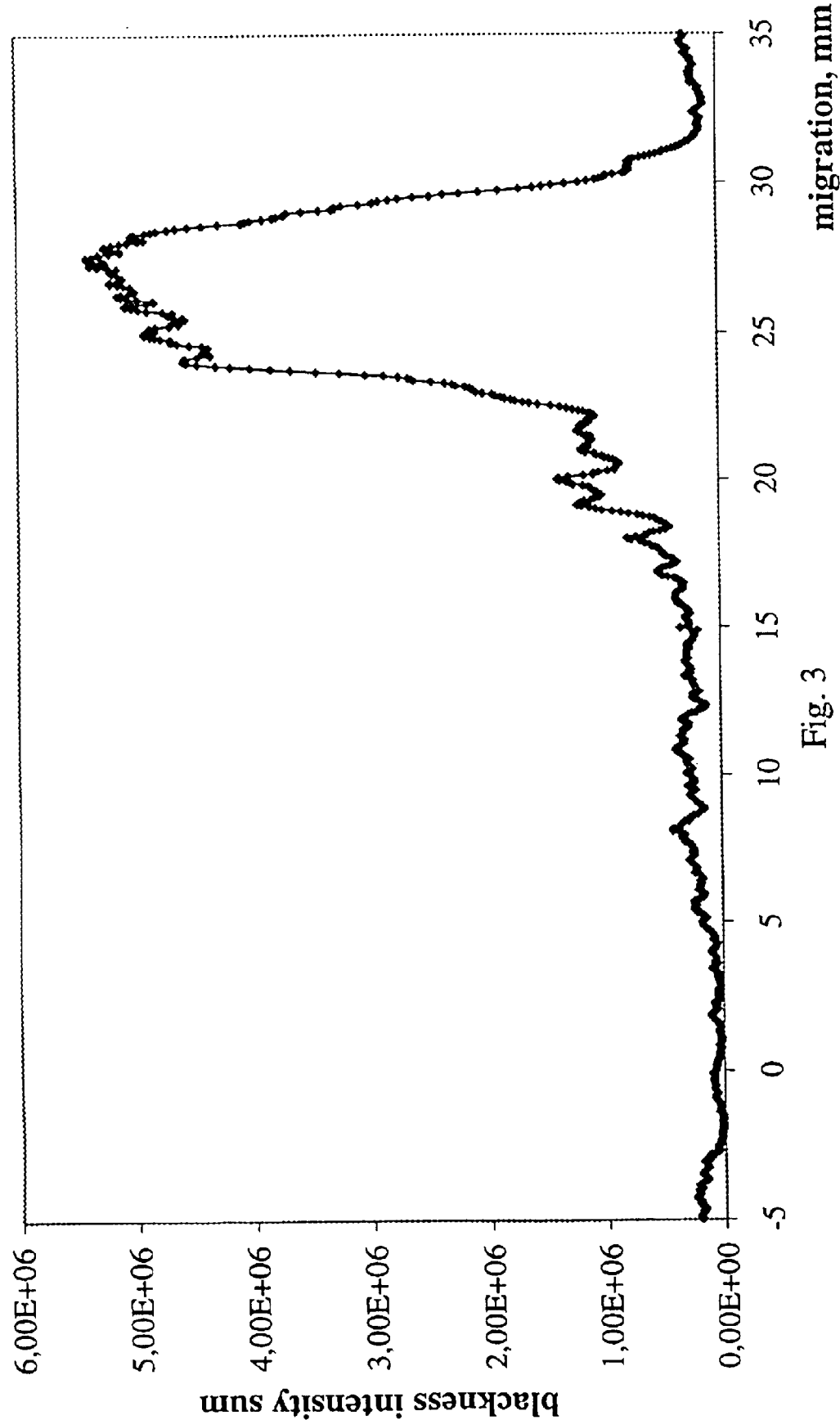
Figure 4:
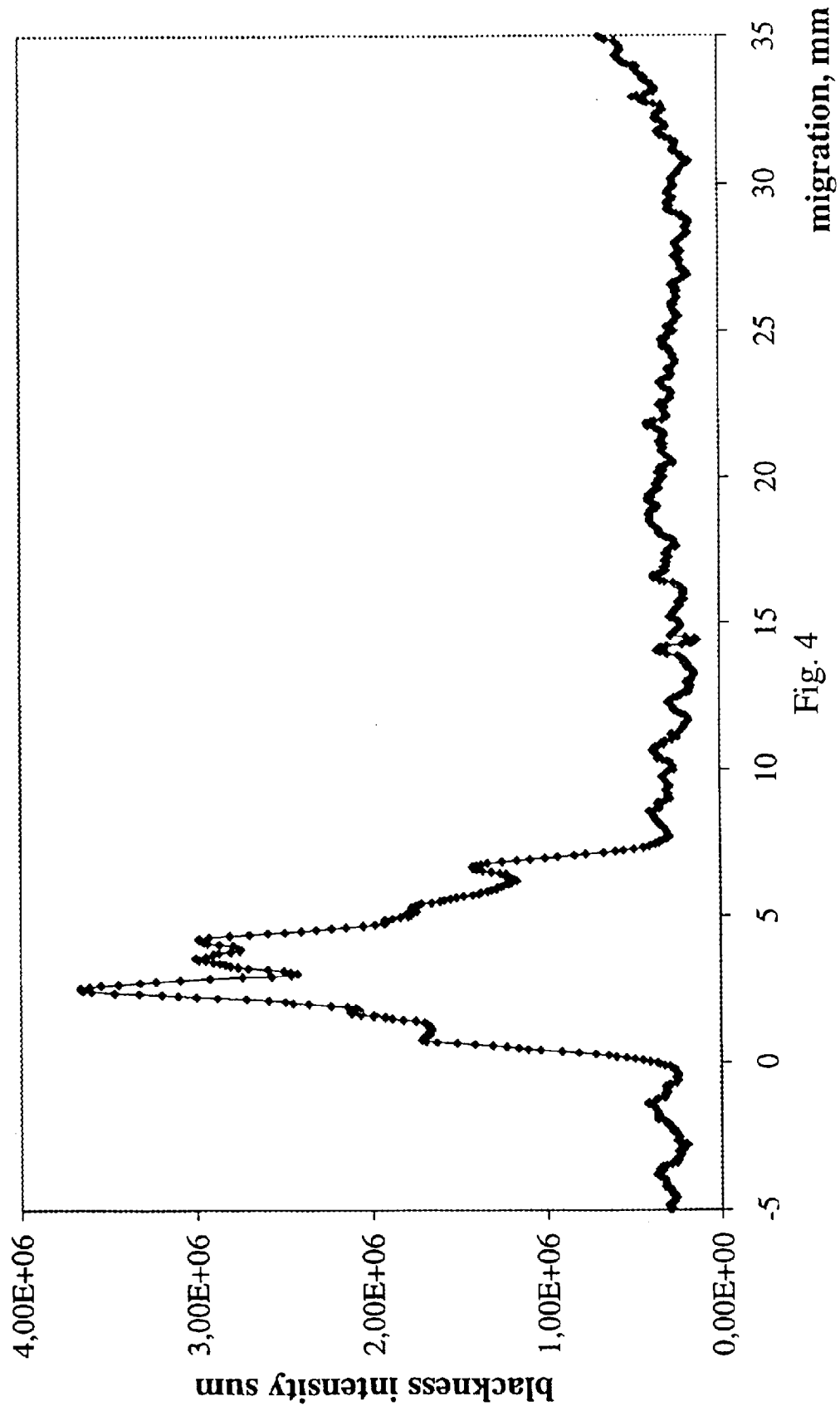
Figure 5:
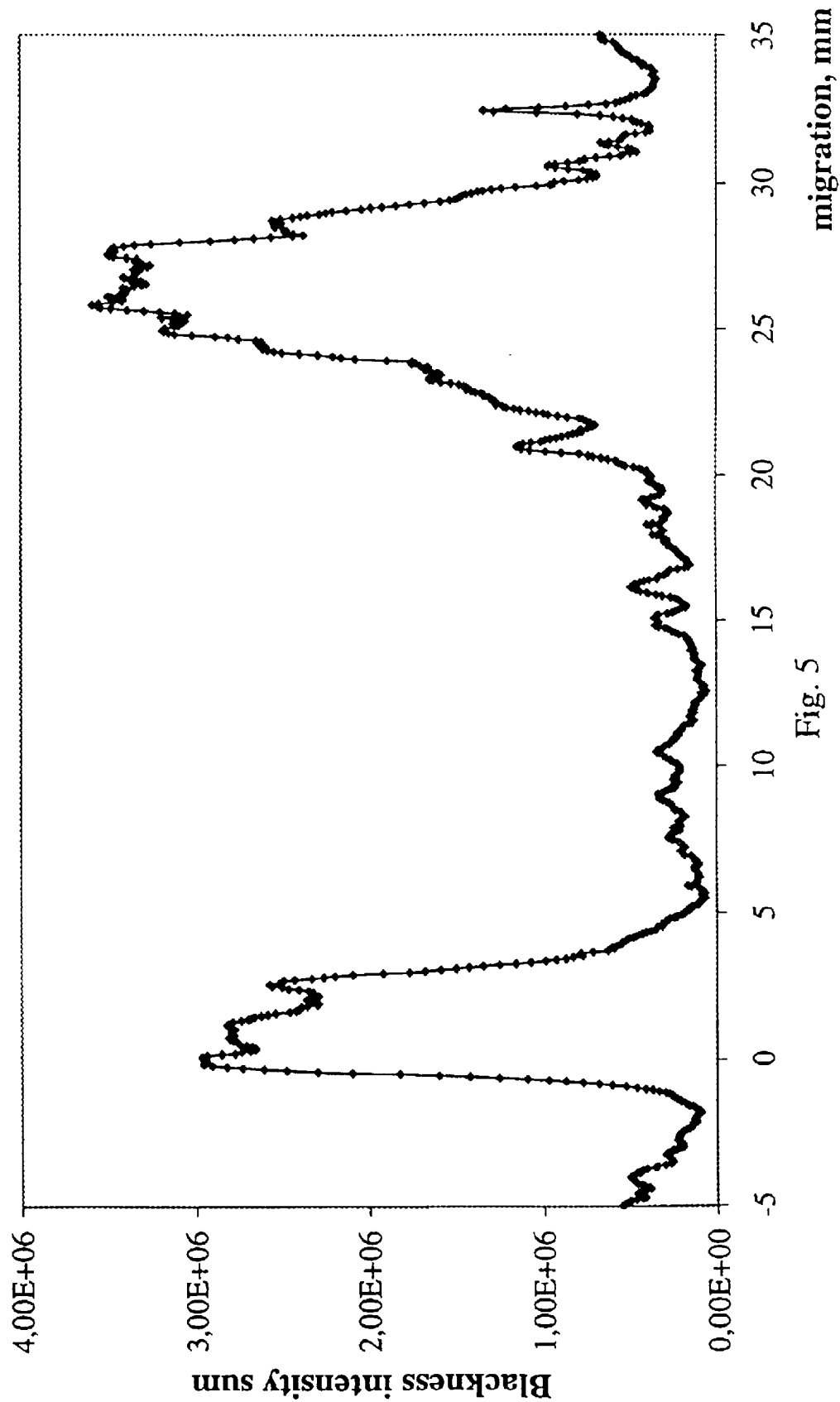

Samples containing 0.7 mg/ml asialo transferrin, pI 5.66 (FIG. 3) or 0.33 mg/ml bovine albumin, pI 4.8 (FIG. 4) or a prepared sample containing 0.5 mg/ml asialo transferrin and 0.33 mg/ml bovine albumin (FIG. 5) were analysed according to the standard protocol above, and the signal intensity curves obtained are shown in FIGS. 3, 4 and 5, respectively.

As demonstrated in these Figures, the method of the invention permits excellent separation between proteins of different isoelectric points.

Chromatographic Quality Test of the Membrane Material

The quality of a chromatographic material can be evaluated by the concept of the theoretical plate. The lower the height of the theoretical plate (HETP), the better the material. The nitrocellulose membrane used above (3 $\mu$m nitrocellulose on polyester backing, Whatman international Ltd, England) was tested by using thin lines of bromophenol blue placed on the membrane, and after the elution had started, pictures were taken by a digital camera (Agfa 1280). Pictures were taken between 2.8–47 mm of migration. The pictures were scanned (Agfa Arcus II scanner), digitilised and processed (Microsoft Excel).

The width of the peaks were measured at the half height ($w_{1/2}$) and the number of theoretical plates (N) were calculated by Formula 1 ($v_r$=migration distance).

$$N = 5.55 \times \left(\frac{V_r}{w_{1/2}}\right)^2 \qquad \text{Formula 1}$$

The theoretical plate height (HETP) was calculated by Formula 2 where L is the migration distance.

$$HETP = \frac{L}{N} \qquad \text{Formula 2}$$

The theoretical plate height depends on the migration distance, as shown in the table below.

| Migration (mm) | $w_{1/2}$ (mm) | HETP ($\mu$m) | Theoretical plates (number) |
|---|---|---|---|
| 2.80 | 1.08 | 75 | 37.3 |
| 10.00 | 1.68 | 51 | 197 |
| 17.30 | 2.00 | 42 | 415 |
| 26.00 | 2.16 | 32 | 804 |
| 32.30 | 2.29 | 29 | 1104 |
| 41.30 | 2.20 | 25 | 1644 |
| 47.00 | 2.52 | 24 | 1931 |

From the table it is seen that for about 40 mm migration, the HETP is about 25 $\mu$m. The migration speed was 0.65 cm/minute. These results are about the same or better than can be obtained by column chromatography.

While the invention has been described and pointed out with reference to operative embodiments thereof, it will be understood by those skilled in the art that various changes, modifications, substitutions and omissions can be made without departing from the spirit of the invention. It is intended therefore that the invention embraces those equivalents within the scope of the claims which follow.

What is claimed is:

1. An ion-exchange chromatographic assay method, comprising the steps of:
    a) providing a polymeric membrane type flow matrix attached to a liquid-impervious backing, which flow matrix permits a capillary force assisted lateral flow therethrough, and at least a part of which flow matrix contains ion-exchange functional groups selected from the group consisting of diethyl aminoethyl (DEAE), trimethyl hydroxypropyl (QA), quaternary aminoethyl (QAE), quaternary aminomethyl (Q), diethyl-(2-hydroxypropyl)-aminoethyl, triethyl aminomethyl (TEAE), triethylaminopropyl (TEAP), polyethyleneimine (PEI), methacrylate, carboxymethyl (CM), orthophosphate (P), sulfonate (S), sulfoethyl (SE) and sulfopropyl (SP), wherein the flow matrix is a porous polymer material with pores in the range of 0.01–20 $\mu$m;
    b) treating the flow matrix to reduce or eliminate nonspecific adsorption properties of the flow matrix;
    c) applying to the flow matrix a sample containing at least two components;
    d) initiating a first lateral flow of aqueous fluid to transport the sample through the flow matrix and chromatographically separate each of the two components from one another and from the sample as they flow along the lateral flow matrix;
    e) interrupting said lateral flow; and either
    f1) detecting at least one of said separated components on the flow matrix in the position reached by the respective component when the flow was interrupted; or
    f2a) initiating a second flow of aqueous fluid to transport the components in a direction substantially transverse to the direction of the first lateral flow,
    f2b) interrupting said second lateral flow; and
    f2c) detecting at least one of said separated components on the flow matrix in the position reached by the respective components when the second lateral flow was interrupted.

2. The method according to claim 1, wherein the separated components are immobilized on the flow matrix in their separated positions prior to detecting said at least one component.

3. The method according to claim 2, wherein the separated components are chemically immobilized on the flow matrix.

4. The method according to claim 2 or 3, wherein the flow matrix is subjected to a staining procedure to detect the component or components.

5. The method according to claim 4, wherein said staining procedure is selected from protein staining, lipid staining, carbohydrate staining, and DNA-staining.

6. The method according to claim 2 or 3, wherein a labeled reactant capable of specifically binding to said at least one component is added to the membrane for the detection thereof.

7. The method according to claim 1, wherein the polymeric membrane type flow matrix is first placed on a flat support surface with the backing contacting the surface.

8. The method according to claim 1, wherein the two components comprise proteins having different isoelectric points.

9. The method according to claim 1, wherein the two components comprise proteins having different isoelectric points, peptides, nucleic acids or polynucleotides.

10. An ion-exchange chromatographic device comprising a polymeric membrane flow matrix attached to a liquid-impervious backing, which flow matrix permits a capillary force assisted lateral flow therethrough and contains ion-exchange functional groups selected from the group consisting of diethyl aminoethyl (DEAE), trimethyl hydroxypropyl (QA), quaternary aminoethyl (QAE), quaternary aminomethyl (Q), diethyl-(2-hydroxypropyl)-aminoethyl, triethyl aminomethyl (TEAE), triethylaminopropyl (TEAP), polyethyleneimine (PEI), methacrylate, carboxymethyl (CM), orthophosphate (P), sulfonate (S), sulfoethyl (SE) and sulfopropyl (SP), sufficient to chromatographically separate each of at least two components from one another and from a sample containing the components as they flow along the lateral flow matrix, wherein the flow matrix is a porous polymer material with pores in the range of 0.01–20 $\mu$m.

11. An apparatus for determining components in a sample, which apparatus comprises the chromatographic device according to claim 10, and means for initiating and maintaining a liquid flow through the membrane.

12. The apparatus according to claim 11, which further comprises reagents for detecting one or more sample components separated in said device, and optionally also reagents for chemically immobilizing the separated components in the device prior to the detection.

13. The apparatus according to claim 11, adapted to chromatographically separate at least two proteins having different isoelectric points from one another and from a sample containing the proteins as they flow along the lateral flow matrix.

14. The apparatus according to claim 11, adapted to chromatographically separate at least two protein components having different isoelectric points, peptide components, nucleic acid components or polynucleotide components from one another and from a sample containing the components as they flow along the lateral flow matrix.

15. An ion-exchange chromatographic assay method, comprising the steps of:
    a) providing a porous polymeric membrane flow matrix attached to a liquid-impervious backing, which flow matrix permits a capillary force assisted lateral liquid flow therethrough, and at least a part of which flow matrix contains ion-exchange functional groups;
    b) treating the flow matrix to reduce or eliminate unspecific adsorption properties of the flow matrix, wherein the treated flow matrix containing ion-exchange functional groups chromatographically separates each of at least two components from one another and from a sample containing the components during their transport along the flow matrix;
    c) applying to the flow matrix a sample containing at least two components;
    d) initiating a first lateral flow of aqueous fluid to transport the sample through the flow matrix and chromatographically separate each of the two components from one another and from the sample during their transport along the flow matrix;
    e) interrupting said lateral flow; and either
    f1) detecting at least one of said separated components on the flow matrix in the position reached by the respective component when the flow was interrupted; or f2a) initiating a second flow of aqueous fluid to transport the components in a direction substantially transverse to the direction of the first lateral flow;

f2b) interrupting said second lateral flow; and f2c) detecting at least one of said separated components on the flow matrix in the position reached by the respective components when the second lateral flow was interrupted.

16. The method according to claim 15, wherein the two components comprise proteins having different isoelectric points.

17. The method according to claim 15, wherein the two components comprise proteins having different isoelectric points, peptides, nucleic acids or polynucleotides.

18. An ion-exchange chromatographic assay method, comprising the steps of:

a) providing a porous polymeric membrane flow matrix attached to a liquid-impervious backing, which flow matrix permits a capillary force assisted lateral liquid flow therethrough, and at least a part of which flow matrix contains ion-exchange functional groups sufficient to chromatographically separate each of at least two components from one another and from a sample containing the components during their transport along the flow matrix, wherein the flow matrix is treated to reduce or eliminate unspecific adsorption properties of the flow matrix;

b) applying to the flow matrix a sample containing at least two components;

c) initiating a first lateral flow of aqueous fluid to transport the sample through the flow matrix and chromatographically separate each of the two components from one another and from the sample during their transport along the flow matrix;

d) interrupting said lateral flow; and either e1) detecting at least one of said separated components on the flow matrix in the position reached by the respective component when the flow was interrupted; or e2a) initiating a second flow of aqueous fluid to transport the components in a direction substantially transverse to the direction of the first lateral flow;

e2b) interrupting said second lateral flow; and e2c) detecting at least one of said separated components on the flow matrix in the position reached by the respective components when the second lateral now was interrupted.

19. The method according to claim 18, wherein the two components comprise proteins having different isoelectric points.

20. The method according to claim 18, wherein the two components comprise proteins having different isoelectric points, peptides, nucleic acids or polynucleotides.

21. An ion-exchange chromatographic device, comprising a porous polymeric membrane flow matrix attached to a liquid-impervious backing, which flow matrix permits a capillary force assisted lateral fluid flow therethrough and contains ion-exchange functional groups sufficient to chromatographically separate at least two components from a sample and from one another during their transport along the flow matrix.

22. The ion-exchange chromatographic device according to claim 21, adapted to chromatographically separate at least two proteins having different isoelectric points from one another and from a sample containing the proteins as they flow along the lateral flow matrix.

23. The ion-exchange chromatographic device according to claim 21, adapted to chromatographically separate at least two protein components having different isoelectric points, peptide components, nucleic acid components or polynucleotide components from one another and from a sample containing the components as they flow along the lateral flow matrix.

* * * * *

UNITED STATES PATENT AND TRADEMARK OFFICE
CERTIFICATE OF CORRECTION

PATENT NO. : 6,902,889 B1
DATED : June 7, 2005
INVENTOR(S) : Jan Carlsson et al.

It is certified that error appears in the above-identified patent and that said Letters Patent is hereby corrected as shown below:

Title page, Item [54] and Column 1, line 1,
Title, change "ANALYTICAL METHOD AND ADVICE" to -- ANALYTICAL METHOD AND DEVICE --.

Column 12,
Line 7, change "now" to -- flow --.

Signed and Sealed this

Twenty-seventh Day of September, 2005

JON W. DUDAS
*Director of the United States Patent and Trademark Office*